(12) United States Patent
Iacono et al.

(10) Patent No.: US 8,158,110 B2
(45) Date of Patent: Apr. 17, 2012

(54) USE OF AEROSOLIZED CYCLOSPORINE FOR PREVENTION AND TREATMENT OF PULMONARY DISEASE

(75) Inventors: Aldo T. Iacono, Hunts Valley, MA (US); Griffith Bartley, Gibson Island, MD (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 235 days.

(21) Appl. No.: 12/433,231

(22) Filed: Apr. 30, 2009

(65) Prior Publication Data

US 2009/0263335 A1    Oct. 22, 2009

Related U.S. Application Data

(63) Continuation of application No. 09/244,792, filed on Feb. 5, 1999, now abandoned.

(51) Int. Cl.
*A61K 9/14* (2006.01)
*A61K 9/12* (2006.01)
*A61K 38/00* (2006.01)
*A61K 38/12* (2006.01)

(52) U.S. Cl. ............. 424/46; 424/45; 424/489; 514/1.6; 514/21.1

(58) Field of Classification Search .................... 424/45, 424/46; 514/9, 11
See application file for complete search history.

(56) References Cited

U.S. PATENT DOCUMENTS

| | | | |
|---|---|---|---|
| 4,996,193 | A | 2/1991 | Hewitt |
| 5,049,388 | A | 9/1991 | Knight et al. |
| 5,342,625 | A | 8/1994 | Hauer et al. |
| 5,635,161 | A | 6/1997 | Adjei et al. |
| 5,654,007 | A | 8/1997 | Johnson et al. |
| 5,665,774 | A | 9/1997 | Armistead et al. |
| 5,688,824 | A | 11/1997 | Williams |
| 5,719,123 | A | 2/1998 | Morley et al. |
| 5,780,014 | A | 7/1998 | Eljamal |
| 5,814,607 | A | 9/1998 | Patton |
| 5,958,378 | A | 9/1999 | Waldrep et al. |
| 6,197,829 | B1 | 3/2001 | Fujii et al. |

(Continued)

FOREIGN PATENT DOCUMENTS

EP    372541    6/1990

(Continued)

OTHER PUBLICATIONS

"ALA Grant Funds Lung Transplant Drug Study", Fall 1998, Lungs at Work (published by the American Lung Association), p. 6.

(Continued)

*Primary Examiner* — Shengjun Wang
(74) *Attorney, Agent, or Firm* — Baker Botts L.L.P.

(57) ABSTRACT

The present invention relates to methods and compositions for prevention of graft rejection in lung transplant recipients and for treatment of subjects with pulmonary disorders. Specifically, the methods and compositions of the invention provide a means for inhibiting immune response mediated inflammatory processes in the lungs. The method of the invention comprises the administration of aerosolized cyclosporine for prevention of acute and/or chronic refractory rejection in lung transplant patients. The invention further provides for the use of aerosolized cyclosporine to treat subjects having immunologically mediated inflammatory pulmonary disorders including, but not limited to, asthma, cystic fibrosis, idiopathic pulmonary fibrosis, chronic bronchitis and allergic rhinitis. The present invention, by enabling a method for the use of aerosolized cyclosporine for inhibiting pulmonary inflammation leading to prevention of graft rejection and treatment of pulmonary disorders, provides a safer and less toxic treatment than those methods that utilize systemic administration of cyclosporine.

56 Claims, 3 Drawing Sheets

Figure 1A:
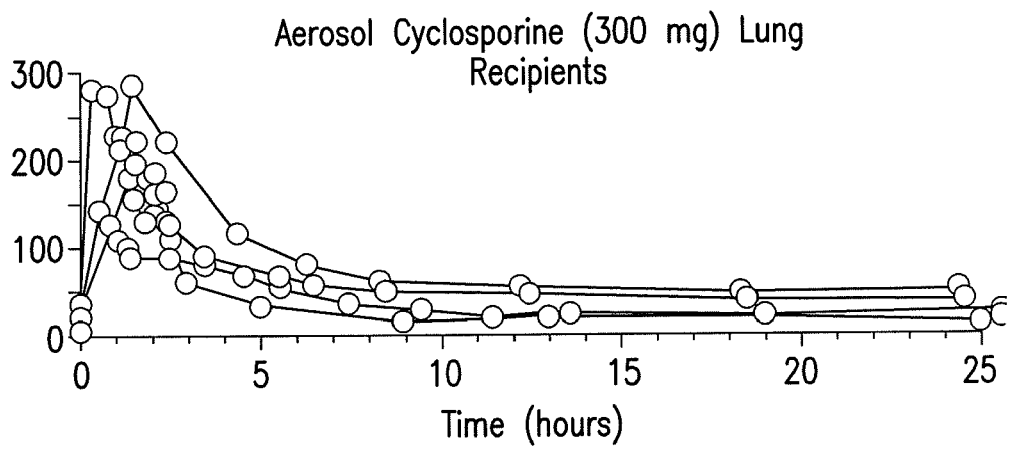

U.S. PATENT DOCUMENTS 6,572,893 B2 6/2003 Gordon et al.

FOREIGN PATENT DOCUMENTS

| TW | WO 98/04279 | 2/1998 |
| WO | WO 98/00111 | 1/1998 |
| WO | WO 98/01147 | 1/1998 |
| WO | WO 99/42124 | 8/1999 |

OTHER PUBLICATIONS

Bolling et al., "Local cyclosporine immunotherapy of heart transplants in rats enhances survival," *J Heart Lung Transplant.* (1991);10(4):577-83.
Bridges et al., "An investigation of some of the factors influencing the jet nebulisation of liposomes," *Int J Pharm.* (2000);204(1-2):69-79.
Burckart et al., "Cyclosporine Administration by Aerosol," *J. Clin. Pharmacol* (1989);29:832-862.
Cahill et al., "Methotrexate for Lung Transplant Recipients with Steroid-Resistant Acute Rejection," *J. Heart and Lung Transplantation* (1996);15:1130-1136.
Cooper, "A working formulation for the standardization of nomenclature and for clinical staging of chronic dysfunction in lung allografts. International Society for Heart and Lung Transplantation," *J Heart Lung Transplant.* (1993);12(5):713-6.
Copeland and Yatscoff, "The Isolation, Structural Characterization, and Immunosuppressive Activity of Cyclosporin G ($Nva^2$-Cyclosprine) Metabolites," *Therapeutic Drug Monitoring* (1991);13:281-288.
Corcoran et al., "Aerosol cyclosporine provides dose dependent improvement in lung function after lung transplantation," *J. Heart Lung Transplant Abstracts* (2003);22:S77.
Decamp, "Inhaled Cyclosporine—A Breath of Fresh Air?" *N. Engl. J. Med.* (2006);354:191-193.
Desai et al., "In vitro evaluation of nebulization properties, antimicrobial activity, and regional airway surface liquid concentration of liposomal polymyxin B sulfate," *Pharm Res.* (2003);20(3):442-447.
Dowling et al., "Aerosolized Cyclosporine as Single-Agent Immunotherapy in Canine Lung Allografts," *Surgery* (1990);108:198-205.
Duncan et al., "Aerosolized cyclosporine for the treatment of refractory chronic lung rejection: a preliminary report," *American review of respiratory disease* (1993 suppl.);147(4) Part 2; A198.
Duncan et al., "Endothelin production, tissue concentration, and receptor expression in acute experimental CsA nephrotoxicity," *Clinical and Investigative Medicine* (1992);15(4 suppl.): p. A155. Abstract No. 977.
Fahr et al., "Liposomal formulations of Cyclosporin A: a biophysical approach to pharmacokinetics and pharmacodynamics," *Crit Rev Ther Drug Carrier Syst.* (2001); 18(2):141-172.
Gilbert et al., "Tolerance of volunteers to cyclosporine A-dilauroylphosphatidylcholine liposome aerosol," *Am J Respir Crit Care Med.* (1997);156(6):1789-93.
Gilbert et al., "Characterization and administration of cyclosporine liposomes as a small-particle aerosol." *Transplantation.* (1993);56(4):974-7.
Glanville et al., "Obliterative Bronchiolitis after Heart-Lung Transplantation: Apparent Arrest by Augmented Immunosuppresion," *Annals of Internal Medicine* (1987);107:300-304.
Griffith et al., "Acute Rejection of Lung Allografts with Various Immunosuppressive Protocols," *Society of Thoracic Surgeons* (1992);54:846-51.
Harrington et al., "Liposomally targeted cytotoxic drugs for the treatment of cancer," *J Pharm Pharmacol.* (2002);54(12):1573-1600.
Iacono et al., "A Randomized Trial of Inhaled Cyclosporine in Lung-Transplant Recipients," *N. Engl. J. Med.* (2006);354:141-150.
Iacono et al., "Dose-Related Reversal of Acute Lung Rejection by Aerosolized Cyclosporine," *Am J Respir Crit Care Med,* (1997);155:1690-1698.
Iacono et al., "Interleukin 6 and Interferon-γ Gene Expression in Lung Transplant Recipients with Refractory Acute Cellular Rejection," *Transplantation* (1997);64:263-269.
Iacono et al., "Aerosolized Cyclosporine in Lung Recipients with Refractory Chronic Rejection," *Am J Respir Crit Care Med* (1996);153:1451-1455.
Kahan, "Cyclosporine," *N Engl J Med.* (1989);321(25):1725-38.
Keenan et al., "Treatment of Refractory Acute Allograft Rejection with Aerosolized Cyclosporine in Lung Transplant Recipients," *J. Thoracic and Cardiovascular Surgery,* (1997);113(2):335-341.
Keenan et al., "Efficacy of Inhaled Cyclosporine in Lung Transplant Recipients with Refractory Rejection: Correlation of Intragraft Cytokine Gene Expression with Pulmonary Function and Histologic Characteristics," *Surgery* (1995);118:385-391.
Keenan et al., "Improved Immunosuppression with Aerosolized Cyclosporine in Experimental Pulmonary Transplantation," *Transplantation* (1992);53:20-25.
Kesten et al., "Treatment of Presumed and Proven Acute Rejection Following Six Mon/ths of Lung Transplant Survival," *Am J Respir Crit Care Med,* (1995);152:1321-1324.
Klyashchitsky et al., "Nebulizer-compatible liquid formulations for aerosol pulmonary delivery of hydrophobic drugs: glucocorticoids and cyclosporine," *J Drug Target.* (1999);7(2):79-99.
Ko et al., "Efficacy of local immunosuppression with intraportal administration of cyclosporine in liver transplantation," *Nippon Geka Gakkai Zasshi (J Jpn Surg. Soc.* ) (1995);96:160-167.
Kumar et al., "Correlation of Blood Levels and Tissue Levels of Cyclosporine with the Histologic Features of Cyclosporine Toxicity," *Transplantation Proceedings* (1988);20:407-413.
Lee et al., "Pharmacokinetics and organ distribution of cyclosporin A incorporated in liposomes and mixed micelles," *Int J Pharm.* (1999);191(2):87-93.
Leonard et al., "PG490-88, a derivative of triptolide, attenuates obliterative airway disease in a mouse heterotopic tracheal allograft model," *J Heart Lung Transplant.* (2002);21(12):1314-8.
Letsou et al., "Pharmacokinetics of liposomal aerosolized cyclosporine A for pulmonary immunosuppression," *Ann Thorac Surg.* (1999);68(6):2044-2048.
Lin et al., "Experimental Heterotopic Heart Transplantation without Ischemia or Reperfusion," *J. Heart Transplantation,* (1990)9:720-723.
Miller and Mason, "Aerosol Deposition of a Propylene Glycol Solution," *Journal of Aerosol Medicine* (1991);4:293-296.
Mitruka et al., "Aerosol Cyclosporine Prevents Acute Allograft Rejection in Experimental Lung Transplantation," *Journal of Thoracic and Cardiovascular Surgery* (1998);115:28-37.
Nunley et al., "Allograft colonization and infections with pseudomonas in cystic fibrosis lung transplant recipients," *Chest* (1998);113(5):1235-43.
Oates et al., "Drug Therapy: Cyclosporine," *New England Journal of Medicine* (1987)321:1725-1738.
O'Riordan, "Formulations and nebulizer performance," *Respir Care.* (2002);47(11):1305-1312.
O'Riordan et al. "Delivery and distribution of aerosolized cyclosporine in lung allograft recipients," *Am J Respir Crit Care Med* (1995);151:516-521.
O'Riordan, et al., "Production of an Aerosol of Cyclosporine as a Prelude to Clinical Studies," *Journal of Aerosol Medicine* (1992);5:171-177.
Paradis et al., "Airway Obstruction and Bronchiolitis Obliterans after Lung Transplantation," *Bronchiolitis* (1993);14:751-763.
Patton, "Deep-lung delivery of proteins," *Modern Drug Discovery* (1998);22:19-28.
Rauscher, "Aerosol Cyclosporine Preserves Lung Function in Transplant Recipients," May 23, 2006, Reuters Health.
Smaldone et al., "Deposition of aerosolized pentamidine and failure of pneumocystis prophylaxis," *Chest.* (1992);101(1):82-87.
Stepkowski et al., "Prolongation of Heterotopic Heart Allograft Survival by Local Delivery of Continuous Low-Dose Cyclosporine Therapy," *Transplantation* (1989);47:17-23.
Stewart et al., "Revision of the 1996 working formulation for the standardization of nomenclature in the diagnosis of lung rejection," *J Heart Lung Transplant.* (2007);26(12):1229-42.
Trulock, "Management of Lung Transplant Rejection," *Chest* (1993);103:1566-1576.
Valentine et al., "Total Lymphoid Irradiation for Refractory Acute Rejection in Heart-Lung and Lung Allografts," *Chest* (1996);109:1184-89.

Waldrep et al., "Pulmonary delivery of beclomethasone liposome aerosol in volunteers," *Tolerance and safety Chest.* (1997);111(2):316-23.

Yousem et al., "A working formulation for the standardization of nomenclature in the diagnosis of heart and lung rejection: Lung Rejection Study Group. The International Society for Heart Transplantation," *J Heart Transplant.* (1990);9(6):593-601.

Zenati et al., "Immunosuppression with Aerosolized Cyclosporine for Prevention of Lung Rejection in a Rat Model," *Eur. J Cardiothorac Surg.* (1990);5:266-272.

Detweiler et al., "Evaluation of the Effects of Cyclosporine Aerosols in Rats Following Repeated Exposure" The Toxicologist, Abstracts of the 29th Annual Meeting of the Society of Toxicology, Feb. 1990., vol. 10, No. 1, pp. 178-EOA.

Aerosol CsA vs. Conventional Rx

— ACsA
— controls

Recipient Survival (%)

Months Post-Transplantation

FIG. 3

USE OF AEROSOLIZED CYCLOSPORINE FOR PREVENTION AND TREATMENT OF PULMONARY DISEASE

RELATED APPLICATIONS

The present application is a continuation of Ser. No. 09/244,792, filed on Feb. 5, 1999, now abandoned, the contents of which are incorporated herein in their entirety.

GRANT INFORMATION

This invention was made with government support under Grant Nos. 1R01HL059490 and 5R01HL059490, awarded by the National Institutes of Health. The government has certain rights in this invention.

1. INTRODUCTION

The present invention relates to methods and compositions for prevention of graft rejection in lung transplant recipients and for treatment of subjects with pulmonary disorders. Specifically, the methods and compositions of the invention provide a means for inhibiting immune response mediated inflammatory processes in the lungs. The method of the invention comprises the administration of aerosolized cyclosporine for prevention of acute and/or chronic refractory rejection in lung transplant patients. The invention is based on the observation that when aerosolized cyclosporine is administered shortly after lung transplantation, the preparation is well tolerated and the rate of acute rejection is substantially reduced, compared to controls that receive conventional oral or intravenous immunosuppression only. The invention further provides for the use of aerosolized cyclosporine to treat subjects having immunologically mediated inflammatory pulmonary disorders including, but not limited to, asthma, cystic fibrosis, idiopathic pulmonary fibrosis, chronic bronchitis and allergic rhinitis. The present invention, by enabling a method for the use of aerosolized cyclosporine for inhibiting pulmonary inflammation leading to prevention of graft rejection and treatment of pulmonary disorders, provides a safer and less toxic treatment than those methods that utilize systemic administration of cyclosporine.

2. BACKGROUND OF THE INVENTION

The long-term success of lung transplantation is currently limited by the high incidence of transplant-related lung disease (Glanville, A. R., et al., 1987, Ann Intern Med 107:300-306; Trulock, E. P., 1993, Chest 103:1566-1576; Kesten, S., 1995, 152: 1321-1324; Paradis, I. et al., 1993, 14:751-763). This complication is related to the transplant recipients' ongoing immune response against donor major histocompatibility antigens. Such an immune response generally leads to persistent acute rejection of the lung allograft which is a predominant risk factor for the subsequent development of chronic rejection and permanent allograft dysfunction and failure resulting in excessive morbidity and mortality. This is a tragic consequence of lung transplantation and for this reason, is a leading area of research in this field. Although the rates of short-term survival after lung transplantation have improved compared to most other solid organ transplants, the therapeutic benefit of lung transplantation is still limited by poor longer-term outcomes principally due to chronic rejection of the transplanted lung.

Patients, whose lung allografts are in acute and/or chronic rejection, are currently treated by a variety of potent immunosuppressive agents, such as azathioprine, tacrolimus, mycophenolate mofetil and cyclosporine, generally given by the intravenous or oral route, that profoundly inhibit the T cell response to donor antigen within the transplanted allograft. Unfortunately, these immunosuppressive agents diminish the patient's ability to mount an effective response to viral, fungal and bacterial pathogens thereby predisposing the patient to life threatening opportunistic infections and other toxic events such as kidney toxicity. Despite usage of conventional systemic (oral or intravenous) immunosuppressive drugs, about 50% of the treated patients develop refractory chronic rejection, characterized histologically by bronchiolitis obliterans, followed by a progressive decline in pulmonary function and eventually respiratory failure and death.

Cyclosporine, an 11-amino acid cyclic polypeptide antibiotic is frequently used to prevent rejection after solid organ transplantation (Kahan, B. D., 1989, N Engl J. Med., 321: 1725-1738; Kumar, M. S. A., et al., Transplant Proc., 20:407-413; Keenan R. J., et al., Transplantation 53:20-25). Cyclosporine acts as an immunosuppressive agent by selectively inhibiting immune responses mediated by T lymphocytes (Iacono, A. T., et al., 1997, Transplantation 64:263-269; Keenan, R. J., 1995, Surgery 118:385-391). Unfortunately, systemic cyclosporine has a narrow therapeutic index, e.g., ratio between toxic and therapeutic doses, and effective immunosuppressive doses often cannot be achieved due to the risk of toxicity to the liver and kidney. In addition, administration of systemic cyclosporine results in a high incidence of infections with viral, bacterial and fungal pathogens.

To date, oral cyclosporine, when combined with azathioprine (AZA) and prednisone, has proven incapable of persistently suppressing the alloresponse to the lung to an extent necessary to provide an optimistic long-term outcome (Griffith, B. P., 1992, Ann Thorac Surg 54:846-51). Other therapies for prevention of transplant rejection include anti-CD3 antibody (OKT3), methotrexate, lymphoid irradiation and mycophenolate mofetil. Unfortunately, even with these treatments clinical efficacy has been disappointing and associated with toxicity (Cahill, B. C., 1996, J Heart Lung Transplant 15:1130-1137; Valentine, V. G., et al., 1996, 109:1184-1189; Copeland, K. R. and Yatscoff, R. W., 13:281-288) Thus, cyclosporine either alone or as part of a multi drug immunosuppressive regimen has been imperfect in preventing both acute and chronic rejection.

Recent data has indicated that immunosuppression by local administration of cyclosporine may be beneficial. For example, using a collagen matrix impregnated with cyclosporine, it was demonstrated that controlled release of low dose cyclosporine, significantly prolonged non-heterologous heart allograft survival with negligible blood and kidney tissue cyclosporine concentrations (Bolling, et al., 1990, J Heart Transplant 9:74-78; Stepkowski, et al, 1989, Transplantation 47:17-23).

While most solid organ transplants are inaccessible to such localized immunosuppress therapy, lung allografts are the exception. Aerosolized pharmacologic agents have direct access to the lung, and there is extensive experience in the use of inhaled β-agonists and nebulized antibiotics. In animal models, aerosolized cyclosporine has been demonstrated to be safe and more effective than systemic cyclosporine in preventing graft rejection (Dowling R. D., 1990, Surgery, 108:198; Zenati, M., 1991, Eur. J. Cardiothor. Surg., 5:266; Keenan, R. J. et al., 1992, Transplantation 53:20-25; Rabinowich H., 1988, Transplant Proc., 20:836). Local delivery of aerosolized cyclosporine has been effectively used to deliver cyclosporine to the lungs of patients with severe chronic graft rejection that was refractory to all previous attempts at control (Burckart, G. J., 1989, J Clin. Pharmaco. 29: 860; Iacono, A. T., et al., 1996, Am. J. Resp. Crit. Care Med., 153:1451-1455). In addition aerosolized cyclosporine was effective as therapy for refractory acute rejection in lung-transplant subjects unresponsive to conventional therapy (O'Riordan, T. G., et al., 1995, Am. J. Respir. Crit. Care Med. 151:516; Iacono, A. T., et al., 1997, Am. J. Resp. Crit. Care Med. 155:1690-1698; Keenen, R. J., et al., 1997, J. Thorac. Cardiovasc. Surg., 1134:335-341).

3. SUMMARY OF THE INVENTION

The present invention provides compositions and methods for using aerosolized cyclosporine for prevention of graft rejection in lung transplant recipients. The invention further provides for the use of aerosolized cyclosporine for amelioration of inflammatory pulmonary disorders including, by way of example and not limitation, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow transplantation or other causes, as well as pulmonary fibrosis resulting from collagen, vascular, and autoimmune diseases such as rheumatoid arthritis and lupus erythematosis.

Delivery of cyclosporine to the transplanted lung by aerosol inhalation achieves higher concentrations in the lung than delivery of the drug by systemic (oral or intravenous) administration, resulting in improved control of rejection, with reduced toxicity due to limited absorption from the lung into the bloodstream.

Accordingly, the methods of the present invention comprise administering aerosolized cyclosporine to a subject having received a lung transplant. To prevent rejection of the lung transplant the cyclosporine is administered directly following the transplant procedure prior to the development of symptoms associated with organ rejection. The administration of aerosolized cyclosporine results in a substantially lower prevalence of acute rejection and development of obliterative bronchiolitis (OB). In addition, cytokines, chemokines and effector molecules normally expressed within the allograft are suppressed, such that the recipient requires less systemic immunosuppression. Moreover, systemic immunocompetence is preserved by maintenance of T-helper cell memory, resulting in a lower incidence of opportunistic and bacterial infection.

In yet another embodiment of the invention, aerosolized cyclosporine is administered to a subject having an inflammatory pulmonary disorder. The method of the invention comprises administering aerosolized cyclosporine to inhibit inflammation in a subject having an inflammatory pulmonary disorder such that the expression of cytokines is modulated and the symptoms of inflammation are ameliorated.

The invention further provides for compositions comprising cyclosporine in a suitable carrier which can be administered to a subject, in aerosolized form, at an effective dose to prevent graft rejection or ameliorate the inflammatory symptoms associated with pulmonary disorders. For subjects with pulmonary disorders, the compositions used in the practice of the invention comprise an effective dose of cyclosporine that is generally lower than the doses reportedly used for treating refractory acute lung rejection or the doses described herein for prevention of lung rejection.

The invention is based on the observation that administration of aerosolized cyclosporine given as a prophylaxis after lung transplantation can prevent acute rejection. The present invention, by providing methods for prevention of graft rejection and amelioration of inflammatory pulmonary disorders using aerosolized cyclosporine, reduces the toxicity and susceptibility to life threatening opportunistic infections associated with systemic use of cyclosporine.

4. BRIEF DESCRIPTION OF THE DRAWINGS

Figure 1B:
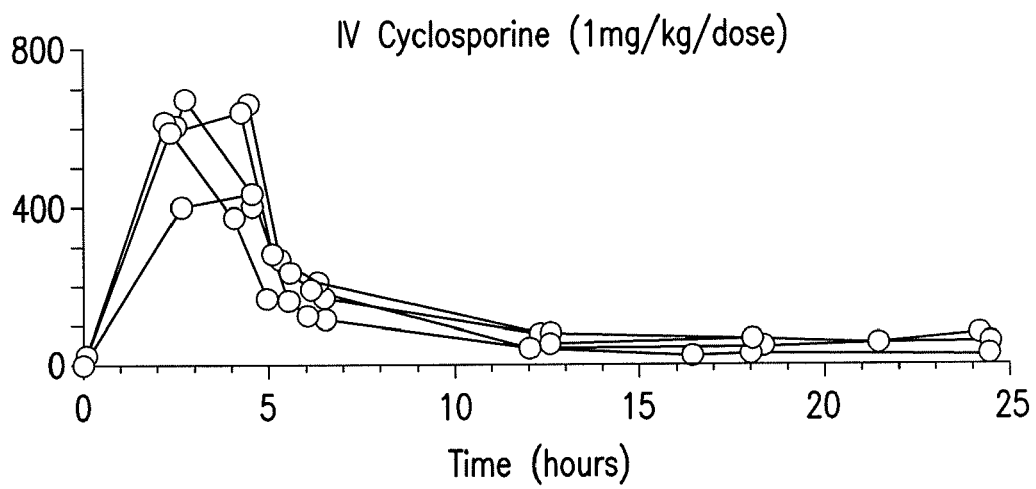
Figure 1C:
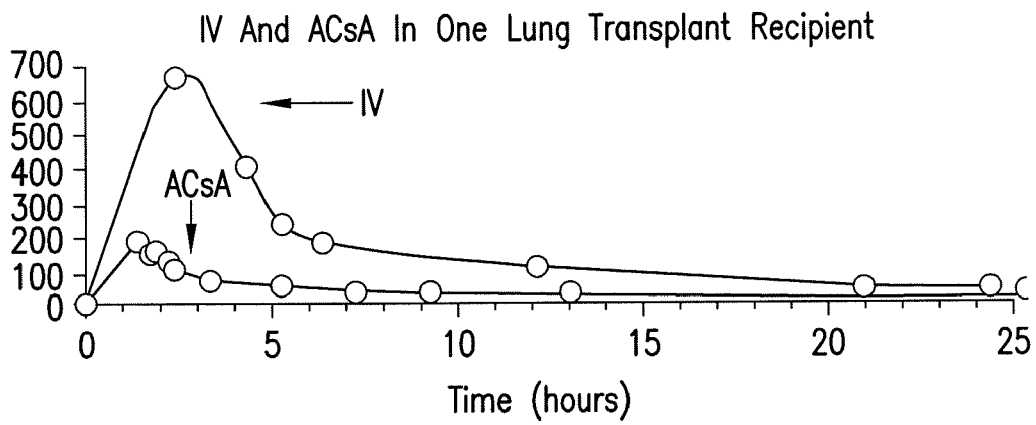

FIGS. 1A, 1B AND 1C. Pharmacokinetics and bioavailability of aerosolized cyclosporine. FIG. 1A. Five subjects studied on average post-operative day number 20.8 underwent blood measurements of cyclosporine after inhalation of a 300 mg dose. FIG. 1B. Subsequently, a dose of intravenous cyclosporine (1 mg/kg over a 4 hour infusion) was administered and blood concentrations of cyclosporine were determined by monoclonal immunoassay over 24 hours following infusion. FIG. 1C compares blood measurements of cyclosporine after inhalation versus intravenous administration.

Figure 2:
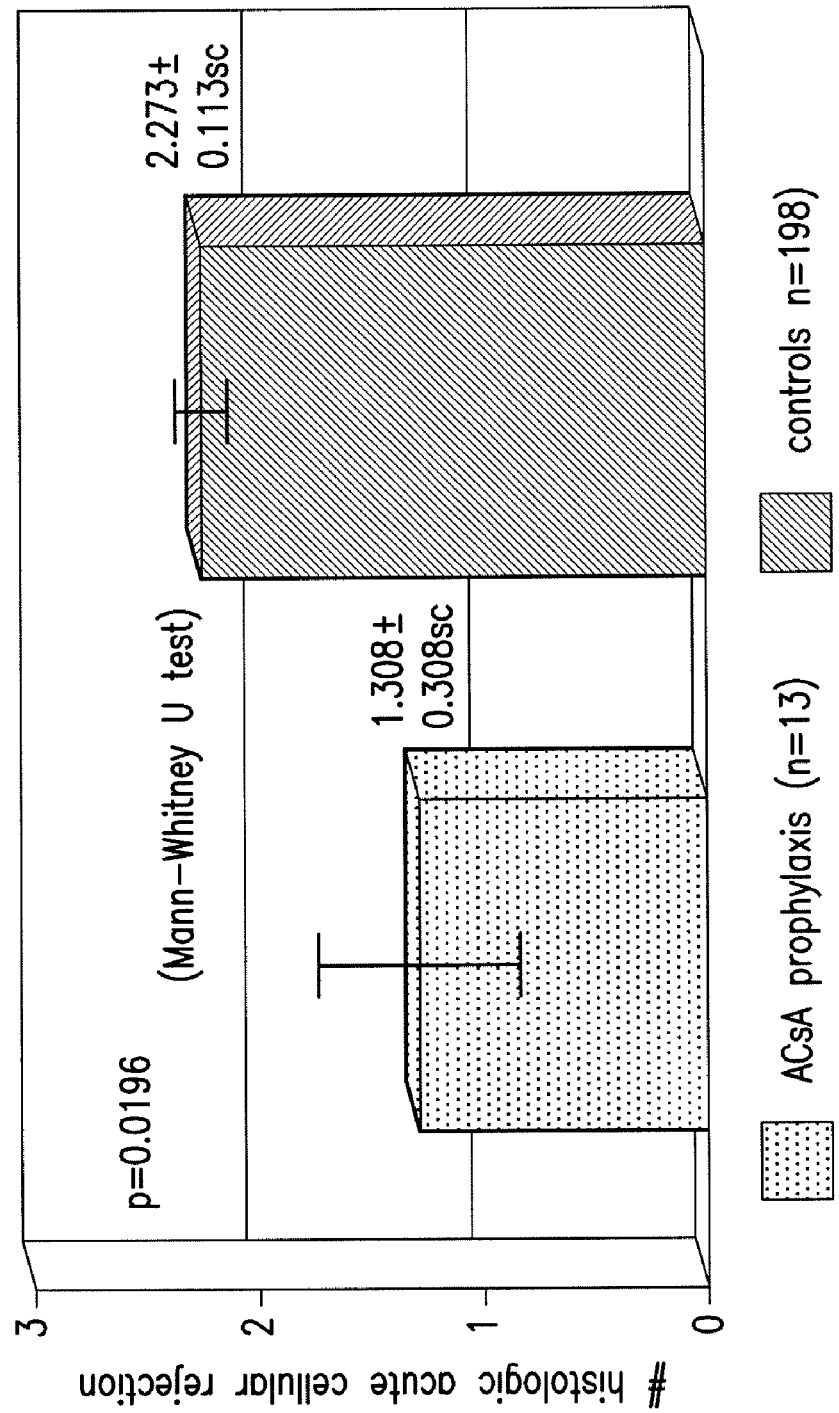

FIG. 2. Acute cellular rejection grade 2 or greater in the first six months post-transplantation. The number of biopsy-proven acute rejection events is decreased in subjects that received aerosolized cyclosporine versus controls that received only standard oral triple drug immunosuppression (2.278 episodes/rejection/subject±0.113 versus 1.308±0.398, p value 0.0196 (Mann-Whitney U test).

FIG. 3. A Kaplan Mayer survival curve in treated subjects versus controls, demonstrating improvement in survival in those subjects that received aerosolized cyclosporine (p=0.014) versus controls receiving standard systemic immunosuppression.

5. DETAILED DESCRIPTION OF THE INVENTION

The present invention relates to methods for preventing graft rejection in lung transplant recipients wherein said methods comprise the administration of aerosolized cyclosporine directly following lung transplantation. The invention further relates to methods for ameliorating inflammation in subjects having inflammatory pulmonary disorders using aerosolized cyclosporine. Subjects treated with aerosolized cyclosporine have reduced pulmonary inflammation due to a cyclosporine mediated decrease in inflammatory cytokines in the lung.

The methods of the invention provide a means for ameliorating pulmonary disorders through direct delivery of the immunosuppressive agent cyclosporine to the lung while avoiding the toxicity associated with systemic use of cyclosporine, or other systemic immunosuppressive drugs that frequently cause toxicity and infection.

5.1. Use of Aerosolized Cyclosporine for Prevention of Rejection in Lung Transplant Recipients The present invention relates to a method for prevention of graft rejection in lung transplant recipients by administration of aerosolized cyclosporine. The present invention is used as a prophylactic means for inhibiting the onset of graft rejection in lung transplant recipients. The method comprises the administration of aerosolized cyclosporine to a transplant recipient directly following transplantation by aerosol inhalation. In a preferred embodiment of the invention, the initial maximum dose of aerosolized cyclosporine is usually administered to the transplant recipient within 10 days following transplantation or prior to the development of any of the symptoms generally associated with lung transplant rejection. The cyclosporine is delivered to the lung of the recipient by inhalation of cyclosporine in aerosol spray form using, for example, a pressurized delivery device or nebulizer. The cyclosporine may be administered in either dry powder or wet form.

Compositions suitable for use in the present invention include compositions comprising cyclosporine in an effective amount to achieve its intended purpose and one or more physiologically acceptable carriers. More specifically, an effective amount means an amount sufficient to prevent development of an immune response that would lead to graft rejection in a lung transplant recipient. An effective dose refers to that amount of cyclosporine sufficient to inhibit an immune response in the lung of the transplant recipient thereby preventing graft rejection. Determination of effective amounts is well within the capability of those skilled in the art.

The effective dose may be determined using a variety of different assays. The progress of the transplant recipient can be determined using assays that include serial transbronchial biopsies to determine the presence and severity of rejection as measured by, for example, a reduction in mononuclear cell inflammatory infiltrate, characteristic of transplant rejection. In such instances, the effective dose of aerosolized cyclosporine is that amount required to sustain a local immunosuppressive effect in the lungs, thereby preventing lung transplant rejection. In addition, assays may be utilized to quantitate the deposition of aerosolized cyclosporine in the lung of the recipient using radionucleotides. Spirometry can be performed following inhalation of aerosolized cyclosporine to assess how much air the lungs can hold as well as how much and how quickly air can be exhaled. A reduction in forced expiratory volume (FEVI) of greater than 15% in conjunction with clinical symptoms of breathlessness indicates the need for reducing the dose of aerosolized cyclosporine. In addition, symptoms of pharyngeal soreness, cough and breathlessness may also indicate the need for reducing the dose of aerosolized cyclosporine.

Serial pulmonary function tests, such as chest radiographs, complete blood counts, assays for electrolytes and creatine levels, and cytokine expression in bronchoalveolar lavage cells, as well as histologic analysis of the lung by transbronchial lung biopsy can be performed to assess efficacy at 1-3 month intervals throughout the course of aerosolized cyclosporine administration.

The amount of composition administered is also dependent on the subject to whom the aerosolized cyclosporine is administered and the judgement of the physician overseeing the subject. It should be noted that the attending physician would know how and when to terminate, interrupt or adjust the treatment to a lower dose due to toxicity. Conversely, the attending physician would also know to adjust treatment to higher levels if the clinical response is not adequate. This can be determined by measurement of the cyclosporine in the lung using known radioisotopic techniques. In addition, adjustments of concomitant administration of additional drugs may be necessary.

In general, the total dose range of cyclosporine should be sufficient to achieve allograft deposition levels ranging between 15 mg and 30 mg in the lung. For example, a dose of between 100-500 mgs of aerosolized cyclosporine may be inhaled, while most preferably the usual dose of aerosolized cyclosporine to achieve deposition in the lung between 15-30 mg is typically 300 mg.

The present invention relates to methods for prevention of graft rejection in lung transplant recipients, therefore, the initial aerosol treatment is administered prior to the development of symptoms normally associated with transplant rejection. In general, administration of aerosolized cyclosporine begins on Day 2-10 post-transplant, while most preferably the treatment begins on Day 5-7 post-transplant. The treatment continues on a daily basis for between 8-15 consecutive days, while most preferably the treatment continues for 10-12 consecutive days. This initial dosing is followed by administration of aerosolized cyclosporine three times weekly for the duration of the life of the transplanted lung.

It is further recommended that infants, children, and subjects with impaired immune systems initially receive lower doses, and they be titrated based on individual clinical response. It may be necessary to use dosages outside the ranges disclosed above in some cases as will be apparent to those of ordinary skill in the art.

In general, the aerosolized cyclosporine is given as the sole immunosuppressive agent if it is found to adequately control rejection. However, aerosolized cyclosporine may be co-administered to a transplant recipient in combination with other immunosuppressive or anti-inflammatory reagents, including but not limited to, oral cyclosporine (2.5-5.0 mg/kg); tacrolimus 0.01-0.04 mg/kg; prednisone 20 mg/kg or 0.3 mg/day. Aerosolized cyclosporine may be give alone if the transplant recipient has a life threatening infection cause by profound inactivation of the immune system due to oral or intravenous immunosuppression, or experiences toxicity, especially to the kidney, due to co-administration of these drugs.

5.2. Use of Aerosolized Cyclosporine for Prevention of Rejection in Organ Transplant Recipients and for Treatment of Immune Disorders In yet another embodiment of the invention, aerosolized cyclosporine can be administered to organ transplant recipients other than lung transplant recipients using a delivery system that utilizes a optimal cyclosporine particle size for systemic delivery of cyclosporine via the lung. Such organ transplants include, but are not limited to, transplants of the liver, kidney, heart and bone marrow. The use of aerosolized cyclosporine provides an effective system for maintaining a steady drug concentration in the bloodstream thereby increasing the efficacy of the cyclosporine and minimizing the toxic side effects associated with cyclosporine.

For pulmonary deposition, the cyclosporine particle size is generally between 1 and 5 microns, a size that generally restricts absorption into the bloodstream. In contrast, where the desired goal is systemic delivery of the cyclosporine via absorption from the lung into the bloodstream, the cyclosporine particle size is reduced to an approximate size of between 0.1 and 2 microns. Methods for producing aerosolized cyclosporine particles of different sizes are routine and well known to those of skill in the art.

Compositions suitable for use in treatment of organ transplant recipients include compositions comprising cyclosporine, in one or more physiologically acceptable carriers, in an effective amount to achieve its intended purpose. More specifically, an effective amount means an amount sufficient to prevent development of an immune response that would lead to graft rejection in a transplant recipient. An effective dose refers to that amount of cyclosporine sufficient to inhibit an immune response in the transplanted organ of the transplant recipient thereby preventing graft rejection. In general, the total dose range of cyclosporine should be sufficient to achieve circulating cyclosporine concentrations of between 50-250 ng/ml, while most preferably the usual dose of cyclosporine is sufficient to achieve circulation levels of 200 ng/ml.

Determination of effective amounts is well within the capability of those skilled in the art. The effective dose may be determined using a variety of different assays. The progress of the transplant recipient can be determined using assays that include biopsies to determine the presence and severity of rejection as measured by, for example, a reduction in mononuclear cell inflammatory infiltrate, characteristic of transplant rejection. In such instances, the effective dose of aerosolized cyclosporine is that amount required to sustain a local immunosuppressive effect in the transplanted organ, thereby preventing organ transplant rejection. In addition, organ function may be monitored using a variety of different assays, the use of which, will depend on nature of the transplanted organ. For example, blood tests may be performed to assay for normal liver or kidney function. In instances where the transplant recipient has received a transplanted heart, an electrocardiogram can be performed to test for normal cardiac function.

In addition to the use of small particle size aerosolized cyclosporine for treatment of non-lung transplant recipients, such delivery systems may be used to treat subjects having T-cell mediated immune disorders such as type IV cell mediated (delayed-type) hypersensitivity, or autoimmune disorders. Autoimmune disorders which may be treated using aerosolized cyclosporine include, for example, systemic lupus erythematosus, myasthenia gravis, Grave's disease, Hashimoto's thyroiditis, rheumatoid arthritis, scleroderma, and pernicious anemia.

The dose of cyclosporine to be used in the method of the invention is an amount sufficient to achieve its intended purpose. More specifically, an effective amount means an amount sufficient to inhibit the immune response associated with the immune disorder.

The effective dose may be determined using a variety of different assays including assays for detection of blood levels of cyclosporine cytokines, and/or the presence of autoreactive T-cells. In such instances, the effective dose of aerosolized cyclosporine is that amount required to sustain an immunosuppressive effect, thereby preventing the symptoms associated with auto-immunity. Determination of effective amounts is well within the capability of those skilled in the art and may be readily ascertained.

5.4. Use of Aerosolized Cyclosporine for Amelioration of Inflammatory Pulmonary Disorders There are a number of significant pulmonary diseases resulting from abnormal accumulations of inflammatory cells in lung tissue. Initially, the inflammatory cells and protein rich fluids accumulate in the lung causing inflammation. If left untreated, the inflammation commonly leads to replacement of normal lung tissue with scarred tissue, which severely limits the ability of the lung to function normally, leading to symptoms of progressive breathlessness, exercise intolerance and eventually a very poor quality of life. Some inflammatory lung diseases, asthma being a common one, cause inflammation and respiratory disability without causing lung scarring. Successful treatment of inflammatory pulmonary disorders can be brought about by techniques which serve to suppress the immune response.

The present invention provides methods for promoting local immunosuppression in the lungs of subjects having pulmonary disorders through inhalation of an aerosol of cyclosporine. The method of the invention comprises the administration of aerosolized cyclosporine to a subject having an inflammatory associated lung disorder. The cyclosporine is delivered to the lung of the subject by inhalation of cyclosporine in the form of an aerosol spray using, for example, pressurized delivery devices or nebulizers. The cyclosporine may be formulated in either a dry powder or liquid form.

Among the pulmonary disorders whose symptoms can be ameliorated by the use of aerosolized cyclosporine are inflammatory pulmonary disorders wherein the symptoms of the disease result from a local immune reaction in the lungs. Examples of such disorders include, but are not limited to, asthma, sarcoidosis, emphysema, cystic fibrosis, idiopathic pulmonary fibrosis, chronic bronchitis, allergic rhinitis and allergic diseases of the lung such as hypersensitivity pneumonitis and eosinophilic pneumonia.

In yet another embodiment of the invention, aerosolized cyclosporine can be administered to patients receiving gene therapy wherein said therapy involves the inhalation of nucleic acids, or recombinantly engineered viruses, encoding a protein of interest. The administration of such nucleic acids or recombinantly engineered viruses can be associated with an inflammatory response in the lungs resulting from the host immune response against the nucleic acid or engineered virus. Thus, aerosolized cyclosporine can be co-administered with nucleic acids or recombinant viruses to reduce the inflammation associated with inhalation of such agents. By reducing the level of inflammation, the therapeutic benefit derived from the gene therapy may be prolonged.

Compositions suitable for use in the present invention include compositions containing cyclosporine and a physiologically acceptable carrier in an effective amount to achieve its intended purpose. More specifically an effective dose refers to that amount of cyclosporine sufficient to inhibit an immune response in the lung of a subject suffering from a pulmonary disorder thereby decreasing the inflammation associated with the disorder. Determination of effective amounts is well within the capability of those skilled in the art and may be readily ascertained.

The effective dose may be determined using a variety of different assays. Transbronchial lung biopsies may be performed to examine whether the lung tissue shows histological evidence of inflammation; and/or assays can be performed to detect cyclosporine mediated reduction in cytokine and chemokine gene expression from bronchoalveolar lavage (BAL) cells and peripheral blood lymphocytes (PBL) of the treated subject. Additionally, assays may be utilized to determine the deposition of aerosol cyclosporine in the lungs using, for example, radionucleotides. Serial spirometry can be used to determine lung volume and flow rate, before and during treatment.

Subject questionnaires with symptom scores will be completed before and during treatment to assess a clinical response. A cardiopulmonary exercise test can be performed at baseline and during therapy to measure oxygen saturations and maximal oxygen consumption during exercise. In such instances, the effective dose of aerosolized cyclosporine is that amount required to sustain a local immunosuppressive effect in the lungs thereby alleviating the symptoms associated with pulmonary inflammation while maintaining acceptable lung volumes and flow rates.

The amount of composition administered is also dependent on the subject to whom the aerosolized cyclosporine is administered, the pulmonary disorder the subject has, the severity of the disorder's symptoms and the judgement of the overseeing physician. In some instances it may be necessary to terminate, interrupt or adjust the treatment to a lower dose due to toxicity as well as adjusting the treatment to higher levels a suitable beneficial response is not obtained.

In general, the total dose range of aerosolized cyclosporine should be sufficient to achieve concentration levels ranging between 5 mg and 30 mg in the lung, while most preferably a dose range sufficient to achieve concentration levels ranging between 5 mg and 15 mg in the lung is desirable. For example, a dose of between 20-400 mg of a aerosolized cyclosporine is administered, while most preferably a dose of aerosolized cyclosporine of between 50-300 mg is administered. Overall, doses of aerosolized cyclosporine may vary depending on the type and extent of lung disease, however it is believed that doses needed to achieve a beneficial response will be less then the doses of aerosolized cyclosporine required to ameliorate transplant related inflammation. It may be necessary to use dosages outside these ranges in some cases, as will be apparent to those of ordinary skill in the art.

Aerosolized cyclosporine may be administered several times per day in small doses to ameliorate relatively mild airway inflammation associated with disorders such as, for example, asthma. Higher doses, given less frequently, may be required to ameliorate more serious inflammation associated with pulmonary disorders such as idiopathic pulmonary fibrosis.

In certain instances, it may be desirable to co-administer to a subject exhibiting pulmonary disorder symptoms, aerosolized cyclosporine in conjunction with an additional agent. Such agents include, for example, antibiotics, antivirals, immunosuppressives or anti-inflammatory agents. Anti-inflammatory drugs include, for example, inhaled steroids 4×220 mgs/puff/day, prednisone 20-60 mg day, methotrexate 5-15 mg/week, azathioprine 50-200 mg/day. Determination of effective amounts of these additional compounds is well within the capability of those skilled in the art.

5.3. Compositions for Aerosolized Delivery of Cyclosporine

The compositions for use in accordance with the present invention may be formulated in a conventional manner using one or more physiologically acceptable carriers or recipients. Cyclosporine for use in the practice of the invention is commercially available and may be obtained from manufacturers, such as Novartis Pharmaceuticals (East Hanover, N.J.).

The cyclosporine can be formulated in pharmaceutically acceptable compositions suitable for delivery to the lungs. Particular formulations include dry powders, liquid solutions or suspensions suitable for nebulization and propellant formulations suitable for use in metered dose inhalers. The preparation of such formulations is well know to those skilled in the art, and is described in U.S. Pat. Nos. 5,814,607 and 5,654,007 the disclosures of which are incorporated herein by reference.

Dry powder formulations will comprise cyclosporine in a dry, lyophilized, form with a particle size within a preferred range for deposition within the lung. Typically the particle size for deposition in the lung will range between 1 and 5 microns. When systemic delivery of the cyclosporine via absorption from the lung into the bloodstream is desired the cyclosporine particle size is generally between 0.1 and 2 microns in size. The preferred size range of particles can be produced using methods such as jet-milling, spray drying and solvent precipitation, for example.

Dry powder devices typically require a powder mass in the range from about 1 mg to 10 mg to produce an aerosolized dose. Thus, the cyclosporine will typically be combined with a pharmaceutically acceptable dry bulking powder. Preferred dry bulking powders include sucrose, lactose, trehalose, human serum albumin (HSA) and glycine. Dry powders can be administered to the subject in conventional dry powder inhalers.

For liquid formulations the cyclosporine can be dissolved in any recognized physiologically acceptable carrier for use in delivery of aerosolized formulations. Such carriers include ethanol, propylene glycol and ethanol-propylene combinations. Although cyclosporine is relatively insoluble in water, it is soluble in lipids and organic solvents, having a solidity of about 80 mg/ml in alcohol at 25° C. In a preferred embodiment the cyclosporine is dissolved in propylene glycol. The choice of propylene glycol is based on its reported use as a solvent to administer aerosolized formulations to individuals (Miller, W. C. et al., 1991, J. Aerosol, Medical. 4:293-297). Such preparations are stable at up to 60 days following preparation.

For administration by inhalation, the compositions for use according to the present invention are conveniently delivered in the form of an aerosol spray administered via pressurized packs or a nebulizer, with the use of a propellant, e.g., dichlorodifluoromethane, dichlorotetrafluoroethane or other suitable gas. Preferably, for incorporation into the aerosol propellant, the cyclosporine of the present invention will be processed into respirable particles as described above for the dry powder formulations. The particles are then suspended in the propellant, typically being coated with a surfactant to enhance their disbursement. In the use of a pressurized aerosol the dosage unit may be determined by providing a valve to deliver a metered amount.

Commercially available jet nebulizers are available and may be used to deliver aerosolized cyclosporine to a subject. Such jet nebulizers include, but are not limited to, those supplied by AeroTech II (CIS-US, Bedford, Mass.). In addition, for delivery of aerosolized cyclosporine to the lungs of a subject an oxygen source can be attached to the nebulizer providing a flow rate of, for example, 10 L/min. In general, inhalation is performed over a 30-40 minute time interval through a mouthpiece during spontaneous respiration.

The present invention provides for novel compositions comprising a suitable carrier and aerosolized cyclosporine in doses sufficient to reduce or ameliorate pulmonary inflammation in subjects having pulmonary disorders. Such doses are lower than those generally used to ameliorate rejection in transplant recipients. In general, the compositions of the invention should be sufficient to achieve concentration levels of between 5-30 mg, while most preferably achieving 5-15 mg in the lung.

6. EXAMPLE

Administration of Aerosolized Cyclosporine as Prophylaxis to Prevent Acute Rejection after Lung Transplantation The following section describes experimental data relating to administration of aerosolized cyclosporine to a transplant recipient directly following lung transplantation. The rate of histological acute rejection for pilot subjects that received aerosolized cyclosporine early after lung transplantation (average day 10) was compared to controls that received conventional oral therapy (tacrolimus, oral cyclosporine, azathioprine and prednisone). As indicated by the data presented, the administration of aerosolized cyclosporine directly following transplantation is capable of preventing acute rejection in the transplant recipient.

6.1. Material and Methods 6.1.1 Subject Population

The subject demographics appear in Table I below. A total of three subjects underwent double lung transplantation (DL), one subject underwent heart-lung transplantation (H-lung), and nine subjects received either a right (RSL) or left (LSL) single lung transplantation.

TABLE I

| S | Sex | Diagnosis | Age | Transplant Type | Recipient CMV Status | Donor CMV Status | Baseline n | Initial Day of aerosol cyclosporine administration | Days of follow up |
|---|---|---|---|---|---|---|---|---|---|
| 1 | M | RE-transplant/OB | 50 | DL | positive | negative | Csa | 31 | 422 |
| 2 | F | CF | 23 | DL | positive | negative | FK | 11 | 200 |
| 3 | F | alpha I antitrypsin re-transplant | 48 | LSL | positive | negative | FK | 8 | 294 |
| 4 | M | emphysema | 66 | LSL | negative | positive | FK | 4 | 181 |
| 5 | F | RE-transplant/OB | 43 | RSL | positive | negative | FK | 6 | 358 |
| 6 | M | emphysema | 67 | RSL | negative | positive | FK | 4 | 245 |
| 7 | F | emphysema | 58 | LSL | positive | positive | FK | 9 | 240 |
| 8 | M | emphysema | 57 | LSL | positive | negative | FK | 7 | 249 |
| 9 | M | emphysema | 66 | LSL | negative | positive | FK | 3 | 210 |
| 10 | M | pulmonary htn | 37 | H-lung | positive | positive | FK | 9 | 265 |
| 11 | M | IPF | 48 | LSL | negative | positive | FK | 11 | 199 |
| 12 | M | emphysema/re-transplant | 57 | LSL | positive | positive | FK | 18 | 71 |
| 13 | M | alpha 1 antitrypsin | 44 | DL | positive | negative | FK | 16 | 310 |

CMV = cytomeglavirus
n = baseline immunosupression
s = subject

In the 13 subjects, administration of aerosolized cyclosporine occurred, on average, ten days following transplantation. Twelve of the thirteen subjects received tacrolimus based immunosuppression. The systemic immunosuppressive drug regimen consisted of oral tacrolimus (0.03 mg/kg/day), or cyclosporine (2.5-5.0 mg/kg/day) azathioprine (1'-2 mg/kg/day), prednisone (0.3 mg/kg/day).

All subjects tolerated the aerosolized cyclosporine therapy. A dose of 300 mg was administered for ten consecutive days followed by 300 mg three days per week on Mondays, Wednesday, and Fridays. Creatinine levels were measured at 30 day intervals during aerosol cyclosporine administration using routine techniques. There have been no subjects that have experienced renal insufficiency as a result of the addition of aerosolized cyclosporine to standard immunosuppressive drug therapies. The average duration of follow-up was 245 days. Rejection was monitored by serial transbronchial lung biopsies performed at 2-3 month intervals in all 13 subjects. Rejection was considered significant if histology showed greater than or equal to grade II acute cellular rejection or active bronchiolitis obliterans according to Yousem, S. A. (1990, J. Heart Lung Transplant. 12:713-716). The rate of rejection in the 13 treated subjects was compared to a group of controls at six months after lung transplantation. The rejection rate was substantially less during follow-up in those subjects treated with aerosolized cyclosporine (see FIG. 2). In addition, treatment has been administered for up to five years thus far and none of the treated subjects, monitored at 2 month intervals since starting aerosolized cyclosporine administration have developed chronic rejection thus far.

6.1.2. Bioavailability Assays

Data regarding pharmacokinetics and bioavailability were obtained using the techniques described in "Pharmacokinetics and Bio-Availability of Aerosolized Cyclosporine in Lung Transplant Recipients" (Vega R. et al., 1998, Resp. and Crit. Care Med. 157:329). Blood concentrations of cyclosporine were determined using a cyclosporine monoclonal immunoassay (TDX; Abbott Laboratories), 24 hours following administration of the aerosolized cyclosporine.

6.1.5. Aerosol Cyclosporine Radioisotope Deposition Studies

The deposited dose of aerosolized cyclosporine was measured in subjects at approximately 60-90 days of administration. A solution of cyclosporine was mixed with 0.3 ml of saline containing a radioisotope tracer ($^{99M}Tc$) and total cyclosporine deposition in the allograft was quantitated using a previously validated technique of O'Riordan, T. G. et al., (1992, J. Aerosol. Med. 5:171-177) and O'Riordan, T. G. et al., (1995, Am. J. Respir. Crit. Care Med. 151:516-521). All subjects deposited the aerosol cyclosporine in their transplanted lung.

6.1.6. Histological Evaluation

Histological diagnosis of lung transplant rejection was made according to Yousem, S. A. et al. (Working Formulation for the Standardization of Nomenclature in the Diagnosis of Lung Rejection, 1990, J. Heart Lung Transplant, 12:713-716). The rate of histological acute rejection events ($\geq$grade II) was analyzed within six months after transplantation.

6.2. Results

None of the subjects to date have developed bronchiolitis obliterans. Two of the subjects died from cytomegalovirus infection and multi-organ system failure.

A Kaplan Mayer survival curve in the 13 treated subjects versus 13 contemporary controls that were matched by type of transplant and age is shown in FIG. 3. Improvement in survival was noted in those subjects that received aerosolized cyclosporine (p=0.014).

6.2.1 Nephrotoxicity is not Observed when Aerosolized Cyclosporine is Given to Prevent Rejection Soon after Transplantation As a measure of toxicity due to systemic absorption of cyclosporine following aerosolized inhalation administration, creatinine levels were compared at initiation of aerosolized cyclosporine administration in transplant recipients and compared with a group of matched contemporary controls that received conventional oral immunosuppressive therapy. The creatinine level at baseline and after a mean of 190 days in transplant recipients and 181 days in control subjects did not differ when aerosolized cyclosporine was added to the immunosuppressive therapeutic regimen (treatment group and controls baseline 0.91 mg/dl±0.22 versus 1.26 mg/dl±0.71, p=0.532; 1.47±0.43 versus 1.58±0.95, p=0.93).

6.2.2. Pharmacokinetics of Aerosol Cyclosporine Given Directly after Lung Transplantation To evaluate pharmacokinetics of cyclosporine when given by aerosol inhalation, bioavailability studies and radioisotope deposition studies were performed. Bioavailability studies demonstrated limited systemic absorption from the lung as compared to the oral administration, and radioisotope studies showed deep lung deposition of the aerosol following inhalation.

Data regarding pharmacokinetics and bioavailability was obtained during the course of the study (FIG. 1). In this study, pharmacokinetics and bioavailability of aerosolized cyclosporine, (300 mg dose) was measured (FIG. 1A). Five transplant recipients studied, on average, by post-operative day 21 underwent blood measurements of cyclosporine after inhalation of a 300 mg dose. All subjects also received oral tacrolimus.

Two days later, a dose of intravenous cyclosporine (1 mg/kg over a 4 hour infusion) was administered and blood concentrations of cyclosporine were determined by monoclonal immunoassay over 24 hours following the infusion (FIG. 1B). Peak concentrations of cyclosporine occurred within the first two hours after inhalation and ranged from 140-280 ng/ml (mean 206.2±56.2). Trough concentrations after 24 hours ranged from 9-44 ng/ml (mean 24.4±14.6). Bioavailability of aerosolized cyclosporine was 9.1%. Absence of high peak levels following inhalation of aerosolized cyclospore (3-4 fold lower than conventional trough levels following an oral dose of cyclosporine) may account for reduced systemic toxicity when cyclosporine is delivered by aerosol inhalation A study was conducted to measure regional deposition and absorption of aerosolized cyclosporine following inhalation of a 300 mg dose in subjects given aerosolized cyclosporine early after transplantation. Regional deposition after a 300 mg dose measured by radioisotope techniques is shown below in Table II.

TABLE II

| | | REGIONAL DEPOSITION | | | | | % REGIONAL VOLUME % | | | |
|---|---|---|---|---|---|---|---|---|---|---|
| Subject | Date | Left Upper | Left Lower | Right Upper | Right Lower | Stomach on Lung | Left Upper | Left Lower | Right Upper | Right Lower |
| 1 | Aug. 29, 1997 | 18.5 | 43.7 | 26.7 | 11.1 | NO | 19.2 | 16.2 | 31.0 | 33.5 |
| 2 | Aug. 29, 1997 | 13.1 | 9.6 | 28.1 | 49.2 | YES | 22.5 | 26.1 | 22.0 | 29.3 |
| 3 | Aug. 28, 1997 | 10.5 | 34.4 | 17.4 | 37.8 | YES | 18.4 | 25.6 | 23.4 | 32.5 |
| 4 | Aug. 26, 1997 | 13.0 | 20.1 | 7.5 | 59.6 | NO | 15.6 | 13.6 | 35.0 | 35.9 |
| 5 | Aug. 26, 1997 | 14.3 | 26.2 | 24.4 | 35.1 | NO | 20.5 | 24.1 | 25.1 | 30.3 |
| 6 | Aug. 26, 1998 | 7.5 | 12.5 | 27.7 | 52.2 | YES | 16.3 | 20.6 | 30.1 | 32.9 |

Thus, the addition of an aerosolized cyclosporine regimen early after lung transplantation decreased the rate of acute rejection. In addition, thus far, no subject has developed chronic rejection, the most tragic complication following lung transplantation that is the principal cause of morbidity and mortality after transplantation. In addition, the drug was tolerated in all subjects and there has been no evidence of nephrotoxicity as creatinine levels did not differ from control subjects. No subject receiving aerosolized cyclosporine has developed renal failure.

7. EXAMPLE

Administration of Cyclosporine for Prevention of Graft Rejection

The following section provides an illustration of the methods and compositions of the invention. Specifically, a protocol for administration of aerosolized cyclosporine to a transplant recipient and methods that may be used for following the progress of the treated subject are provided.

7.1. Chemistry, Manufacturing and Control Procedures for Aerosolized Cyclosporine Cyclosporine powder for manufacturing the solution for nebulization used in this protocol is obtained from Novartis Pharmaceutical, East Hanover, N.J., (300 mg of cyclosporine powder, aerosolized in 4.8 ml propylene glycol). Propylene glycol is a recognized physiologically acceptable solvent which is used as a vehicle to deliver other aerosolized formulations such as inhaled pentamidine. New lots of cyclosporine require a purity and identity check using high performance liquid chromatography. Cyclosporine for aerosol delivery is prepared in a standard concentration of 62.5 mg/ml. The specific stability of cyclosporine in propylene glycol has been tested by high pressure liquid chromatographic assay of cyclosporine against methanolic standards. Reverse phase C18 chromatography was performed with a mobile phase of 67% acetonitrile at 1.0 ml/min, column heated at 70° C., with ultraviolet detection at 214 nm. These tests have indicated that the preparation is 84% stable at up to 60 days following preparation. Lots of cyclosporine in propylene glycol which are >30 days past the date of preparation should be destroyed, and fresh lots are spot checked to be sure deterioration had not occurred by chance.

7.2. Method of Aerosolized Cyclosporine Administration During Mechanical Ventilation The recipient subject should be on assist control mode and relaxed. Sedation can be used if necessary. Tidal volume and frequency can be consistent with conventional settings that were being used in the intensive care unit for ventilatory support. The nebulizer with cyclosporine solution is prepared in the usual manner and the nebulizer is triggered by the ventilator's nebulizer trigger system (Bennett 7200). The humidifier circuit should be bypassed during the nebulization, which will increase nebulizer efficiency by 50%. The nebulization is carried out to dryness.

7.3. Delivery Schedule and Dose of Aerosols

Recipient subjects are previously exposed to an aerosol of propylene glycol to assess their tolerance to the aerosol. A small number of subjects (2-7%) are expected to be intolerant, in which case a different solvent is employed. Aerosols containing cyclosporine are given using a commercially available jet nebulizer (AeroTech II, CIS-US, Bedford, Mass.). Inhalation is performed for 20-30 minutes through a mouthpiece during spontaneous respiration. A commercially available high efficiency particulate air filter is used to ensure absence of environmental contamination (AeroStar, Bio-Safety Systems, San Diego, Calif.).

Aerosolized cyclosporine administration begins on post-transplant Day 6 and continues dosing daily, for 11 consecutive days. This initial daily dosing, followed by three times weekly has been successfully used, as described in Section 6, supra. Following the initial daily dosing, aerosols are administered on Mondays, Wednesdays, and Fridays for convenience. In spontaneously ventilated subjects, spirometry will be obtained prior to and immediately after treatment during the first 3 days with a Morgan spirometer interfaced with a Medical Graphics Model 1070 pulmonary function analyzer (350 Oak Grove Parkway, St. Paul, Minn.). Quantitation of deposition of aerosolized cyclosporine using radionucleotides is calculated on the seventh day of aerosol administration. Changes in the inhaled dose of aerosolized cyclosporine from a baseline of 300 mg is dependent on measured allograft deposition as follows: subjects that deposit between 10-15 mg, increase aerosolized cyclosporine to 400 mg; 5-10 mg, increase aerosolized cyclosporine to 500 mg. Further increments are based on subsequent deposition studies. Changes to doses are made if higher than expected allograft cyclosporine deposition is measured after a 300 mg dose as follows: 25-30 mg, decrease aerosolized cyclosporine to 200 mg; 30-35 mg, decrease aerosolized cyclosporine to 100 mg. In double lung recipients, deposition of inhaled cyclosporine can vary between the right and left allografts. In such bilateral transplant recipients, the lung that deposits the lower cyclosporine concentration is used to make the necessary dose adjustments.

Spirometry is performed immediately after inhalation of aerosolized cyclosporine during the initial 10 days of treatment, and a reduction in the Forced Expiratory Volume (FEVI) of greater than 15% on two separate occasions, associated with clinical symptoms of breathlessness is grounds for reducing the dose of aerosolized cyclosporine. The nebulizer charge is reduced by 100 mg per day and spirometry is repeated immediately after the dose. The minimum dose of aerosolized cyclosporine is 100 mg.

Symptoms of pharyngeal soreness, cough and breathlessness may occur in transplant recipients during the course of aerosolized cyclosporine administration. If intolerable side effects occur, the dose of the aerosol preparation is reduced or discontinued; but, the attending physician is encouraged to reinstitute administration at a later time. Should the recipient's condition change, the physician can use any clinically indicated intervention that is appropriate for the given situation, including adjustments of concomitant treatment with other drugs.

7.4. Detection and Grading of Rejection and Measurement of Allograft Function Blinded histopathologic interpretation of biopsy specimens is conducted using the accepted standard grading system of the International Society for Heart and Lung Transplantation. Successful prevention of rejection is defined as transbronchial biopsy with a histologic grade of acute rejection that is $\leq$ grade I (Yousem, S. A. et al., 1990, J. Heart Lung Transplant 12:713-716).

Spirometry (FVC, $FEV_1$, FEF25-75) is performed at baseline and at 6 week intervals throughout treatment. By establishing baseline spirometric indices for each recipient prior to aerosolized cyclosporine administration, and comparing these with values measured during administration, individual regression lines of the $FEV_1$ can be calculated for each subject. Analysis of the rate of decline of the $FEV_1$ and histopathological assessment of the allograft allows diagnosis of chronic rejection.

7.5. Cytokine and Chemokine Gene Expression

Cytokine and chemokine gene expression are measured from bronchoalveolar lavage cells (BAL) and peripheral blood lymphocytes (PBL) in treated subjects and the dose of aerosolized cyclosporine is adjusted accordingly. BAL cells and PBL are isolated immediately prior to aerosolized cyclosporine administration at approximately day 7 and at the time of bronchoscopy and cytokine mRNA expression is determined at baseline. The effects of local enhanced immunosuppression with aerosolized cyclosporine on the expression of IL-2, IL-6, IL-10, TGF-$\beta$, IFN-$\gamma$, inducible nitric oxide synthase (iNOS), Granzyme and perforin are tested. Cellular gene expression of the various cytokines are measured at 8-week intervals, at the time BAL cells are isolated after each protocol bronchoscopy, and at various time intervals throughout the treatment period. An increase in expression of the cytokines serves as an indicator that an increase in the dose of cyclosporine is required.

Unseparated BAL cells and Ficoll-Hypaque isolated PBMC are snap frozen before and after a short stimulation of one hour with phytohaemagglutinin (PHA). Stimulation with PHA permits detection of the presence of IL-2 mRNA in unseparated BAL cells from rejecting allografts but does not stimulate up-regulation of IL-2 in BALs from transplant recipients during quiescence or in naive PBL cells. A similar experience was reported by J. Andersson et al., (1994, Immunology 83:16-24) who found that preactivated T-cells, after a short course of stimulation (two hours, anti-CD3), exhibited intracellular cytokine production, while naive cells required 24-hour stimulation.

Cytokine gene expression is qualitatively measured by application of RT-PCR. Total RNA is extracted from unstimulated BAL cells and peripheral blood lymphocytes using the RNAzol B modified method (Chirgwin, J. M. et al., 1979, Biochemistry 18:5294) The RNA concentration is determined by spectrophotometry. The complementary DNA (cDNA) was synthesized by transcription from RNA in the presence of human placental RNA-ase inhibitor, Inmol/L deoxynucleoside triphosphates, oligonucleotide deoxythymidine primer, murine leukemia virus reverse transcriptase and reverse transcriptase buffer. The RT PCR of the resulting cDNA is performed according to well established protocols known in the art. Aliquots of the cDNA are amplified using primers specific for cytokines measured.

Amplification is carried out for 30 cycles on a Perkin-Elmer Cetus Model 480 thermal cycler (Norwalk, Conn.). As an internal control for quality and potential degradation of RNA, all RNA samples are assessed for the constitutive gene $\beta$-actin cyclophilin. For negative controls, PCR amplification is performed with sterile water substituted for cDNA. PCR products are analyzed by electrophoresis in 2% agarose gels and visualized by ethidiurn bromide staining. RT-PCR is carried out in the presence of $^{32}P$-deoxycytidine triphosphate labeled primers. The product of the amplification is electrophoresed on an 8% polyacrylamide gel that is dried and submitted to autoradiography. The amounts of radioactivity incorporated in the PCR product are then counted with a $\beta$-scanner.

The results are expressed as a ratio of cytokine to actin, and cytokine to cyclophilin, expression. The cytokine to actin ratio is determined at the time of initiation and during aerosolized cyclosporine administration. Changes in cytokine gene expression over time are correlated by linear regression with the dose of aerosolized cyclosporine deposited in the allograft and the grade of histologic inflammation associated with acute rejection.

7.6. Reduction of Maintenance Doses of Prednisone and Tacrolimus

In many instances, aerosolized cyclosporine is administered with other immunosuppressive drugs, such as prednisone, azathioprine, tacrolimus, as well as oral cyclosporine. Systemic (oral) immunosuppression is gradually reduced for subjects to whom aerosolized cyclosporine is administered that are free of histologic rejection. Should surveillance biopsies fail to show significant rejection ($\geq$ grade I acute rejection) on two consecutive occasions, prednisone doses are reduced from 0.3 mg/kg/day to 0.2 mg/kg/day until two additional biopsies are free of rejection, and then the dose drops to 0.1 mg/kg/day. The prednisone dose remains at this level unless rejection occurs at which time it is increased to 0.3 mg/kg/day to begin the cycle again. After completion of the prednisone taper, tacrolimus blood levels are gradually reduced by approximately 5 ng/ml at 4-month intervals to maintain blood levels at a minimum of 7.5-10 ng/ml. Should two consecutive biopsies show significant rejection during tacrolimus taper (acute rejection ≧grade 2 or active obliterative bronchiolitis), tacrolimus blood levels are increased to the previous baseline (15-20 ng/ml).

7.7. Monitor for Immunosuppressive Drug Toxicity

Throughout the course of treatment recipient subjects are monitored monthly for evidence of toxicity due to immunosuppression. One or more of the following variables are monitored in each subject: 1) serum creatinine; 2) blood pressure; 3) tremor, headache, paresthesia, confusion and psychiatric disorders, such as depression and anxiety; 4) nausea, dysphagia, constipation, vomiting, gastritis, gastric and duodenal ulcer, oral moniliasis, diarrhea; 5) hirsutism and gingival hyperplasia; 6) hepatic dysfunction; 7) diabetes mellitus, gout, and hypercholesterolemia; 8) osteoporosis by quantitating bone mineral density by bone density scan, stress fractures by radioisotopic bone scan if clinically indicated, arthritis and arthralgias, muscle pain and myopathy, and 9) post-transplant lymphoproliferative disease and other neoplasms. Should the subject show evidence of toxicity, the dose of aerosolized cyclosporine will be adjusted accordingly.

7.8. Monitor for Infection within and Outside of the Allograft

The number of infectious complications, including pneumonia, emphysema, sinusitis, septicemia, abscesses, and urinary tract, viral, pulmonary and systemic fungal, and skin and wound infections that occur during the treatment are also monitored.

Peripheral blood samples are collected pretransplant (baseline), 2 weeks posttransplant, every 2 months, and when recipients are evaluated for infection and rejection. The response to the following three different types of stimuli can be assayed: 1) stimulation by recall antigens (RA) (TT 4 µg/ml, CMV 1:200 dilution) to determine the function of CD4+ T cells responding to nominal antigen presented by autologous APCs; 2) stimulation by a pool of MHC disparate cells to assess the response of T-h cells (CD4+ and CD8+) to direct presentation of alloantigen (ALLO), 3) and the polyclonal stimulation of T cells by mitogens PHA and conconavalin A mitogen (ConA).

7.9. Aerosol Studies: Measuring Drug Deposition Using Radionucleides

Total aerosol deposition in the subject is measured using a mass balance technique. Using this method, the amount of radioactivity inhaled by the subject and the amount exhaled are measured using filters. In the case of a small particle nebulizer such as the AeroTech II (Cis-Us, Bedford, Mass.) (used to deliver aerosolized cyclosporine), the dose deposited in the recipient subject is near equivalent to the total lung dose, because pharyngeal/laryngeal deposition is minimal. The difference between these two measurements is the amount deposited in the subject. The advantage of this approach is that it avoids the use of attenuation coefficients which may be difficult to interpret in the context of non-uniform aerosol deposition. The radioactive exposure is equivalent to typical x-rays of the ribs (100-200 millirads).

A recipient subject, wearing nose clips, inhales a nebulized radioactive solution from a typical nebulizer circuit. A low resistance absolute filter is attached to the expiratory part of the nebulizer. This filter is designated as the "exhalation filter. However, in addition to capturing all the particles that are exhaled by the subject, it will also capture those particles that are produced by the nebulizer during the expiratory phase of respiration, i.e., particles that were never inhaled. These latter particles are referred to as "the leakage" of the nebulizer. In order to determine the amount inhaled and "the leakage", a calibration run is necessary that necessitates duplicating the subject's breathing pattern. The output of the subject's nebulizer (µCi/min) is determined by interposing a filter between the nebulizer and the subject's mouth ("inspiratory filter") and capturing the aerosol that would be inhaled. Aerosol produced by the nebulizer, but not inhaled into the inspiratory filter (i.e., during expiration) is captured on the "leakage filter." The inspiratory filter captures all of the particles that would have been inhaled by the subject. During the calibration run, because there is no exhalation of particles from the subject, all the particles on the filter at the expiratory port are the equivalent of the amount that would have been "leaked." The amount of radioactivity on the leakage filter is subtracted from the amount on the subject's exhalation filter (from the subject's original treatment run) to give the amount truly exhaled. After decay correction, the amount deposited is calculated as the difference between the amount of cyclosporine inhaled and the amount exhaled. The same nebulizer is used for the treatment and the calibration run since significant inter-nebulizer variability may occur. VEmon represents an estimate of minute ventilation (VE) used to monitor breathing pattern during aerosol delivery. It consists of minute ventilation plus the gas used to run the nebulizer during expiration, and serves as an indicator that the breathing pattern was controlled during both the calibration (left) and treatment runs (right) (Smaldone G C, Dickinson G, 1992, Chest 101: 82-87.)

The mass balance technique measures the dose deposited in the subject. To determine the regional distribution of the dose (right vs. left lung or central airways versus lung periphery), gamma camera imaging of deposited radioactivity is needed. When particles are inhaled by a subject, they will either be exhaled or be retained (deposited). In healthy subjects, a uniform deposition pattern within the lungs indicates that most of the particles have deposited in small peripheral airways or alveoli by means of gravitational sedimentation. A common non-uniform pattern seen in healthy subjects due to inertial impaction, is the peri-hilar pattern in which particles have deposited predominantly in the typical uniform and non-uniform deposition patterns. The aerosol deposition patterns are superimposed on an outline of the whole lung, which was generated using a Xenon ($^{133}$Xe) equilibrium scan. $^{133}$Xe is a gas with a long half-life (5.3 days) which, when breathed to equilibrium measures regional lung volume.

Therefore, using regions of interest based on the $^{133}$Xe image, it is possible to facilitate comparison between serial studies in the same subject, or make intersubject comparisons of the distribution of deposited particles in the lung and airways (Iacono et al., Am. J. Respir. Crit. Care Med. 55:1690-1698). Following a $^{133}$Xe equilibrium scan, using a computer in series with a gamma camera, regions are drawn around each lung which is called the whole lung zone and another pair of regions are drawn which centered over the large central airways comprising 33% of the entire lung area, is called the central zone. The area remaining after the central zone is deducted from the whole lung zone and is designated the peripheral zone. To describe the regional pattern of deposition of an inhaled aerosol, labeled with $^{99m}$Tc, and allow intersubject comparisons, the ratio between central (C) and peripheral (P) lung counts (C/P) is calculated in a manner which normalized for differences in relative lung thickness by dividing the C/P $^{99m}$Tc counts by the C/P 133Xe counts. The ratio defined the specific C/P ratio (sC/P). Using the resulting sC/P values, a ratio of 1.0 indicates equal deposition in all lung regions. Because the central lung region outlines both central airways and the lung parenchyma surrounding them, an sC/P ratio of unity reflects predominantly alveolar deposition. Increasing deposition in the proximal airways results in increasing sC/P ratios greater than unity. Therefore, determination of the sC/P ratio allows quantification of initial deposition patterns and comparisons between subjects.

7.10. Aerosol Cyclosporine Kinetic Studies

Cyclosporine pharmacokinetic studies may be performed at, for example, Week 12 in recipient subjects. After obtaining a baseline 3.0 ml blood sample, the subject receives 1.0 mg/kg cyclosporine intravenously as a 4 hour infusion. Additional blood samples are drawn at 2.0, 4.0, 5.0, 6.0, 12.0, 18.0 and 24 hours after initiation of the infusion. On day number 2 of the study, after the final 24.0 hour sample is obtained, a 300 mg dose of aerosolized cyclosporine or placebo is given, with blood samples taken at 0.25, 0.5, 0.75, 1.0, 2.0, 4.0, 6.0, 8.0, 12.0, 18.0, and 24.0 hours after initiation of the aerosolized dose. Samples are analyzed for both cyclosporine and tacrolimus. The intravenous cyclosporine dosage allows the calculation of cyclosporine total body clearance, elimination half-life and volume of distribution. Having those results, one can accurately calculate the amount of cyclosporine that was absorbed from the aerosolized dose in those subjects on the active drug, as well as calculate the absorption rate constant for drug deposited in the lungs.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

The invention claimed is:

1. A method for preventing chronic graft rejection in a human lung transplant recipient, comprising administering to a transplant recipient, by inhalation, an aerosolized composition comprising an effective dose of cyclosporine, wherein said aerosolized composition is administered at least three times per week over a period of at least about 3 months, and wherein said transplant recipient does not have grade II or greater acute cellular rejection or active bronchiolitis obliterans.

2. The method of claim 1, wherein a dose of cyclosporine administered is sufficient to achieve deposition levels ranging between 5 mg and 15 mg in a lung.

3. The method of claim 1, wherein a dose of cyclosporine administered is sufficient to achieve deposition levels ranging between 15 mg and 30 mg in a lung.

4. The method of claim 1, wherein the total dose of cyclosporine administered is sufficient to achieve deposition levels ranging between 15 mg and 45 mg per week in a lung.

5. The method of claim 1, wherein the total dose of cyclosporine administered is sufficient to achieve deposition levels ranging between 45 mg and 90 mg per week in a lung.

6. The method of claim 1, wherein a dose of cyclosporine administered is sufficient to achieve circulating cyclosporine levels ranging between 50 ng/ml and 250 ng/ml.

7. The method of claim 1, wherein a dose of cyclosporine administered is between 100 mg and 500 mg.

8. The method of claim 1, wherein a dose of cyclosporine administered is between 20 mg and 400 mg.

9. The method of claim 1, wherein a dose of cyclosporine administered is between 50 mg and 300 mg.

10. The method of claim 1, wherein the first administration occurs within 10 days of transplantation.

11. The method of claim 1, wherein the aerosolized composition is co-administered with an effective amount of one or more other agents selected from the group consisting of an immunosuppressive agent and an anti-inflammatory agent.

12. The method of claim 1, wherein the cyclosporine is administered as a dry powder.

13. The method of claim 1, wherein the cyclosporine is dissolved in an organic solvent.

14. The method of claim 1, wherein the cyclosporine is dissolved in propylene glycol.

15. A method for preventing chronic graft rejection in a human lung transplant recipient, comprising administering to a transplant recipient, by inhalation, an aerosolized composition comprising an effective dose of cyclosporine, wherein said aerosolized composition is administered at least three times per week over a period of at least 6 months, and wherein said transplant recipient does not have grade II or greater acute cellular rejection or active bronchiolitis obliterans.

16. The method of claim 15, wherein a dose of cyclosporine administered is sufficient to achieve deposition levels ranging between 5 mg and 15 mg in a lung.

17. The method of claim 15, wherein a dose of cyclosporine administered is sufficient to achieve deposition levels ranging between 15 mg and 30 mg in a lung.

18. The method of claim 15, wherein the total dose of cyclosporine administered is sufficient to achieve deposition levels ranging between 15 mg and 45 mg per week in a lung.

19. The method of claim 15, wherein the total dose of cyclosporine administered is sufficient to achieve deposition levels ranging between 45 mg and 90 mg per week in a lung.

20. The method of claim 15, wherein a dose of cyclosporine administered is sufficient to achieve circulating cyclosporine levels ranging between 50 ng/ml and 250 ng/ml.

21. The method of claim 15, wherein a dose of cyclosporine administered is between 100 mg and 500 mg.

22. The method of claim 15, wherein the total a dose of cyclosporine administered is between 20 mg and 400 mg.

23. The method of claim 15, wherein a dose of cyclosporine administered is between 50 mg and 300 mg.

24. The method of claim 15, wherein the first administration occurs within 10 days of transplantation.

25. The method of claim 15, wherein the aerosolized composition is co-administered with an effective amount of one or more other agents selected from the group consisting of an immunosuppressive agent and an anti-inflammatory agent.

26. The method of claim 15, wherein the cyclosporine is administered as a dry powder.

27. The method of claim 15, wherein the cyclosporine is dissolved in an organic solvent.

28. The method of claim 15, wherein the cyclosporine is dissolved in propylene glycol.

29. A method for preventing chronic graft rejection in a human lung transplant recipient, comprising administering to a transplant recipient, by inhalation, an aerosolized composition comprising an effective dose of cyclosporine, wherein said aerosolized composition is administered at least three times per week over a period of at least 12 months, and wherein said transplant recipient does not have grade II or greater acute cellular rejection or active bronchiolitis obliterans.

30. The method of claim 29, wherein a dose of cyclosporine administered is sufficient to achieve deposition levels ranging between 5 mg and 15 mg in a lung.

31. The method of claim 29, wherein a dose of cyclosporine administered is sufficient to achieve deposition levels ranging between 15 mg and 30 mg in a lung.

32. The method of claim 29, wherein the total dose of cyclosporine administered is sufficient to achieve deposition levels ranging between 15 mg and 45 mg per week in a lung.

33. The method of claim 29, wherein the total dose of cyclosporine administered is sufficient to achieve deposition levels ranging between 45 mg and 90 mg per week in a lung.

34. The method of claim 29, wherein a dose of cyclosporine administered is sufficient to achieve circulating cyclosporine levels ranging between 50 ng/ml and 250 ng/ml.

35. The method of claim 29, wherein a dose of cyclosporine administered is between 100 mg and 500 mg.

36. The method of claim 29, wherein a dose of cyclosporine administered is between 20 mg and 400 mg.

37. The method of claim 29, wherein the total a dose of cyclosporine administered is between 50 mg and 300 mg.

38. The method of claim 29, wherein the first administration occurs within 10 days of transplantation.

39. The method of claim 29, wherein the aerosolized composition is co-administered with an effective amount of one or more other agents selected from the group consisting of an immunosuppressive agent and an anti-inflammatory agent.

40. The method of claim 29, wherein the cyclosporine is administered as a dry powder.

41. The method of claim 29, wherein the cyclosporine is dissolved in an organic solvent.

42. The method of claim 29, wherein the cyclosporine is dissolved in propylene glycol.

43. A method for preventing chronic graft rejection in a human lung transplant recipient, comprising administering to a transplant recipient, by inhalation, an aerosolized composition comprising an effective dose of cyclosporine, wherein said aerosolized composition is administered at least three times per week over a period of at least 5 years, and wherein said transplant recipient does not have grade II or greater acute cellular rejection or active bronchiolitis obliterans.

44. The method of claim 43, wherein a dose of cyclosporine administered is sufficient to achieve deposition levels ranging between 5 mg and 15 mg in a lung.

45. The method of claim 43, wherein a dose of cyclosporine administered is sufficient to achieve deposition levels ranging between 15 mg and 30 mg in a lung.

46. The method of claim 43, wherein the total dose of cyclosporine administered is sufficient to achieve deposition levels ranging between 15 mg and 45 mg per week in a lung.

47. The method of claim 43, wherein the total dose of cyclosporine administered is sufficient to achieve deposition levels ranging between 45 mg and 90 mg per week in a lung.

48. The method of claim 43, wherein a dose of cyclosporine administered is sufficient to achieve circulating cyclosporine levels ranging between 50 ng/ml and 250 ng/ml.

49. The method of claim 43, wherein a dose of cyclosporine administered is between 100 mg and 500 mg.

50. The method of claim 43, wherein a dose of cyclosporine administered is between 20 mg and 400 mg.

51. The method of claim 43, wherein a dose of cyclosporine administered is between 50 mg and 300 mg.

52. The method of claim 43, wherein the first administration occurs within 10 days of transplantation.

53. The method of claim 43, wherein the aerosolized composition is co-administered with an effective amount of one or more other agents selected from the group consisting of an immunosuppressive agent and an anti-inflammatory agent.

54. The method of claim 43, wherein the cyclosporine is administered as a dry powder.

55. The method of claim 43, wherein the cyclosporine is dissolved in an organic solvent.

56. The method of claim 43, wherein the cyclosporine is dissolved in propylene glycol.

* * * * *

UNITED STATES PATENT AND TRADEMARK OFFICE
CERTIFICATE OF CORRECTION

PATENT NO. : 8,158,110 B2
APPLICATION NO. : 12/433231
DATED : April 17, 2012
INVENTOR(S) : Iacono et al.

Page 1 of 1

It is certified that error appears in the above-identified patent and that said Letters Patent is hereby corrected as shown below:

On the Title Page

Item (75) Inventors: Aldo T. Iacono "Hunt Valley, MA (US)"
Should read:
Item (75) Inventors: Aldo T. Iacono "Hunt Valley, MD (US)"

Signed and Sealed this
Third Day of April, 2018

Andrei Iancu
*Director of the United States Patent and Trademark Office*